United States Patent [19]
Freeman

[11] Patent Number: 6,074,408
[45] Date of Patent: Jun. 13, 2000

[54] MODULAR MEDICAL INSTRUMENT AND METHOD OF USING SAME

[76] Inventor: Kenneth V. Freeman, P.O. Box 157, Laconia, N.H. 03247

[21] Appl. No.: 09/170,580

[22] Filed: Oct. 13, 1998

Related U.S. Application Data

[60] Provisional application No. 60/063,279, Oct. 27, 1997.

[51] Int. Cl.[7] .................................................. A61B 17/28
[52] U.S. Cl. ........................................................ 606/205
[58] Field of Search .................................. 606/108, 110, 606/113, 114, 205, 206, 104

[56] References Cited

U.S. PATENT DOCUMENTS

| | | | |
|---|---|---|---|
| 5,224,954 | 7/1993 | Watts et al. | 606/205 |
| 5,238,002 | 8/1993 | Devlin et al. | 606/205 |
| 5,325,866 | 7/1994 | Krzyanowski | 606/205 X |
| 5,782,747 | 7/1998 | Zimmon | 606/104 |
| 5,810,876 | 9/1998 | Kelleher | 606/205 |

OTHER PUBLICATIONS

Circon ACMI Endourology Product Catalog, May 1993, Circon Corporation Storz, The World of Endoscopy, Extract from Catalog Endoscopic Surgery, 2nd edition, Jan. 1993.

*Primary Examiner*—Michael Buiz
*Assistant Examiner*—Vikki Trinh
*Attorney, Agent, or Firm*—Bourque & Associates, P.C.

[57] ABSTRACT

A modular medical instrument is used with an endoscope or other similar medical instrument to perform medical procedures, such as endoscopy, bronchoscopy, and laparoscopy. The modular medical instrument comprises an elongated instrument device, an optional port fitting detachably coupled to the instrument device, and an actuator handle detachably coupled to the port fitting. The instrument device includes an elongated guide member, an inner actuation cable slidably disposed within the guide member, and an instrument device head assembly disposed at a distal end of the guide member and actuation cable. The guide member preferably has a smooth outer surface to facilitate insertion within the instrument channel of an endoscope or similar medical device. In one example, the instrument device head assembly includes a grasping device, such as biopsy forceps. The biopsy forceps device includes first and second jaws pivotably coupled to a body member, which is detachably coupled to an adapter at the distal end of the guide member. The actuation cable includes first and second portions or wires extending through the body member and coupled to the respective jaws such that relative movement of the actuation cable with respect to the body member causes the jaws to open and close. Each of the components or subassemblies of the modular medical instrument are detachable for cleaning and/or replacement.

20 Claims, 6 Drawing Sheets

FIG. 16

MODULAR MEDICAL INSTRUMENT AND METHOD OF USING SAME

RELATED APPLICATIONS

This application claims the benefit of U.S. Provisional Patent Application Ser. No. 60/063,279 filed Oct. 27, 1997, fully incorporated herein by reference.

FIELD OF THE INVENTION

The present invention relates to modular medical instruments and methods of using same and in particular, relates to modular medical instruments having grasping devices, such as a forceps device.

BACKGROUND OF THE INVENTION

Endoscopy is a well known medical procedure that allows relatively noninvasive exploration and surgical procedures to be conducted within a patient while transmitting an image from within the patient to a monitor that is viewed by the surgeon or other medical personnel. A conventional endoscope includes an elongated scope body that is inserted into a body lumen or passageway and a handle that controls insertion of the scope body. A fiber optic sensor or video camera chip is disposed at the distal end of the elongated scope body, for transmitting an image of the body passageway to a monitor or video screen.

An instrument channel extends through the elongated scope body to receive different types of medical instruments or accessories used to perform the medical procedures within the patient's body. The medical instruments that are commonly used with endoscopes include, but are not limited to, foreign body graspers, wire snares, biopsy forceps, retrieval baskets, cautery tools, probes and other similar medical instruments or accessories. The endoscope allows the operator to observe the medical instrument in the body passageway during the medical procedure without having to perform invasive general surgery on the patient. Endoscopes are used for a number of different types of procedures including, but not limited to, gastrointestinal endoscopy, bronchoscopy, cystoscopy and laparoscopy.

The elongated medical instruments used with endoscopes present a number of problems to hospitals and other health care facilities. Initially the medical instruments were designed to be reusable. Although reusing the instruments appeared to be cost effective to the hospital or health care facility, the necessary repeated cleanings and reprocessing of the reusable instruments has been a problem. The elongated structure and the inability to disassemble the medical instruments make it particularly difficult to access the channels and other areas to be cleaned within the medical instrument. In order to effectively clean the medical instruments and to take advantage of the maximum number of uses from each instrument, the health care facility must train and control the medical personnel responsible for carrying out the extensive cleaning process. The difficulty of properly training and controlling the medical personnel responsible for cleaning and reprocessing the medical instruments lowers the confidence level in the sanitation of the instruments.

In an attempt to eliminate the problems associated with cleaning these reusable medical instruments, disposable or "single-use" medical instruments were designed. The disposable medical instruments, however, created a number of additional problems related to the proper disposal of medical waste. The health care facility must now control the proper disposal of these disposable or "single-use" devices, which involves additional costs as well as the ecological impact of medical waste disposal.

As a result of the increased medical waste and costs associated with disposal, many medical facilities began reusing the disposable or "single-use" devices. These disposable medical instruments, however, are not designed for reuse and are more easily worn and damaged if used more than once, possibly causing complications during use. Additionally, properly cleaning such devices is a serious problem and concern.

One type of medical instrument commonly used with an endoscope or the like is a biopsy forceps device. The conventional biopsy forceps device includes an elongated outer body portion made of a stainless steel coil, an inner stainless steel actuation cable extending within the outer body, and a head assembly disposed at a distal end of the outer body and inner cable. The head assembly includes jaws coupled to the inner cable with a clevis and 2 links to allow the jaws to be opened and closed by movement of the inner cable relative to the outer body portion. The typical biopsy forceps head assembly is soldered or brazed to the outer body and cannot be disassembled for cleaning and/or replacement. If one component of the biopsy forceps device is damaged, the medical facility must dispose of the entire device or return the device to the manufacturer for repair. The soldering or brazing of the head assembly components also causes annealing of the stainless steel material in the outer body coil, resulting in a susceptibility to kinks and therefore decreasing the usable life of the biopsy forceps device.

Another disadvantage of the conventional biopsy forceps devices is the connection of the jaws to the clevis and two links that are used to open and close the jaws. The clevis is typically attached by being soldered or brazed to the actuation cable extending within the outer body portion. The heat generated by the soldering or brazing causes annealing in the stainless steel actuation cable, resulting in cable breakage and a decreased usable life of the biopsy forceps device. The links of the biopsy forceps device also typically become lodged with debris, causing the physician to use a greater force to operate the device and eventually damaging the device. The clevis and links also inhibit the fluid passage through the outer jacket and prevent adequate cleaning of the device. Attempts at eliminating the clevis and links have resulted in a biopsy forceps device that is more easily damaged and not able to be reused.

Another problem with existing medical instruments is the excessive wear caused by inserting and moving the medical instrument through the instrument channel of the endoscope, which is often an articulated endoscope having a bend. Damage to the endoscopes by these medical instruments or accessories results in additional costs for repair and/or replacement of the endoscopes. When using the conventional biopsy forceps device, for example, the outer diameter of the outer jacket and head assembly as well as the length of the head assembly cause friction as the biopsy forceps device is pushed through the instrument channel of an endoscope or the like.

Accordingly, a need exists for a medical instrument, such as a biopsy forceps device, that can more easily be cleaned by flushing with a fluid and reused without being worn and damaged. The need also exists for a medical instrument, for use with an endoscope or other similar medical device, that is designed to be more easily pushed through the instrument channel in the endoscope or the like without causing excessive wear and damage to the endoscope.

SUMMARY OF THE INVENTION

The present invention features a modular medical instrument comprising an elongated guide member having a proximal end and a distal end and a channel extending from the proximal end to the distal end. The modular medical instrument further comprises an inner actuation cable slidably disposed within the channel in the elongated guide member and an instrument head assembly disposed at the distal end of the inner actuation cable and extending from the distal end of the elongated guide member. An actuator handle is detachably coupled to the proximal end of the elongated guide member and to the proximal end of the inner actuation cable such that the actuator handle moves the inner actuation cable within the channel in the elongated guide member to actuate the instrument head assembly.

The present invention also features a modular medical instrument assembly comprising an elongated guide member, a port fitting adapted to be detachably coupled to a proximal end of the elongated guide member, and an actuator handle adapted to be detachably coupled to either the port fitting or the proximal end of the elongated guide member. The port fitting includes at least one flush port for providing fluid communication with the channel of the elongated guide member.

The preferred embodiment of the handle actuator includes a handle body having a first end adapted to be detachably coupled to either the port fitting or the proximal end of the elongated guide member, and having a second end, for engagement by a hand of a user. The handle actuator also includes a sliding member slidably disposed on the handle body. The sliding member is adapted to be coupled to the proximal end of the actuation cable and is adapted to be engaged by the hand of the user such that relative movement between the sliding member and the handle body causes relative movement of the inner actuation cable within the channel of the elongated guide member.

The present invention also features a forceps device for use with a modular medical instrument. The forceps device comprising a body member having a first end and a second end. First and second forceps jaws are pivotably coupled to the first end of the body member and have respective first and second tangs. An actuation cable extends through the second end of the body member. The actuation cable has a first portion at one end coupled to the first tang of the first forceps jaw and a second portion at the one end coupled to the second tang of the second forceps jaw. Movement of the actuation cable relative to the body member causes the forceps jaws to open and close.

According to the preferred embodiment, the actuation cable includes a wound stainless steel cable having at least first and second wire portions extending through the second end of the body member. The first wire portion extends through the first tang of the first forceps jaw and the second wire portion extends through the second tang of the second forceps jaw. The first and second wires extend back through the second end of the body member and are coupled to the wound stainless steel cable.

According to the preferred embodiment, the elongated guide member includes a stainless steel spring coil and an FEP heat shrink outer jacket disposed over the stainless steel spring coil. The elongated guide member further includes an adapter secured to the stainless steel spring coil at the distal end of the elongated guide member. The body member of the forceps device is detachably coupled to the adapter.

DESCRIPTION OF THE DRAWINGS

FIGS. 13A and 3B are top and side views, respectively, of a body member of the biopsy forceps device, according to the present invention;

DESCRIPTION OF THE INVENTION

Figure 1:
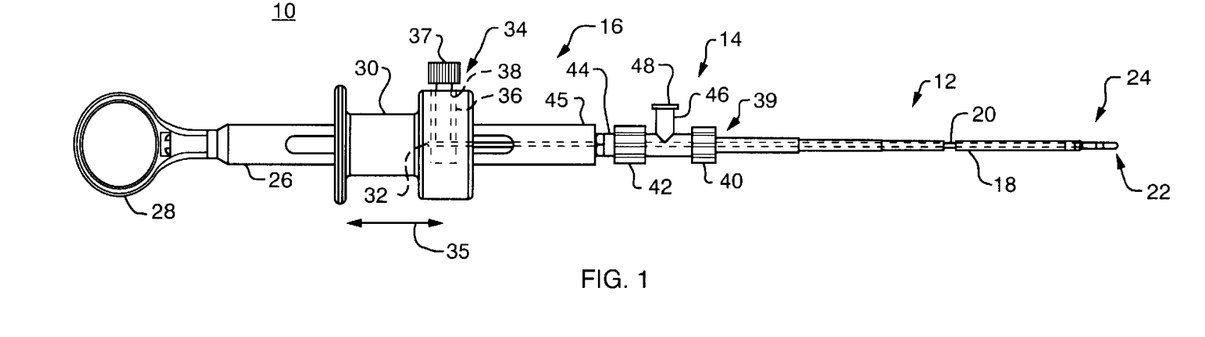
FIG. 1 is a side view of a modular medical instrument according to one embodiment of the present invention.

A modular medical instrument 10, FIG. 1, according to the present invention, is used with an endoscope or other similar medical device. The modular medical instrument 10 is used to perform relatively noninvasive medical procedures within a body passageway of an individual including, but not limited to, gastrointestinal endoscopy, bronchoscopy, and laparoscopy. In these applications, the modular medical instrument is used to remove tissue or other objects from within the passageway. The present invention contemplates using the modular medical instrument and the concepts of the present invention with other types of medical devices and procedures such as vascular and other procedures.

The modular medical instrument 10 comprises an elongated instrument device 12, an optional port fitting detachably coupled to the instrument device 12, and an actuator handle 16 detachably coupled to the port fitting 14. The instrument device 12 includes an elongated guide member 18, an inner actuation cable 20 slidably disposed within the guide member 18, and an instrument device head assembly 22 disposed at a distal end 24 of the guide member 18 and actuation cable 20. The instrument device 12 is inserted within the instrument channel of an endoscope or similar medical device. The actuator handle 16 moves the inner actuation cable 20 within the guide member 18 to actuate the head assembly 22, which is used to perform the procedure, e.g. grasping objects, within the patient. Each of the components or sub-assemblies—the guide member 18, actuation cable 20 and head assembly 22, the port fitting, and the handle 16—are detachable for cleaning and/or replacement.

The handle actuator 16 includes a handle body 26 having a thumb ring 28 coupled at one end of the handle body 26. In one embodiment, a spool sliding member 30 is slideably disposed on the handle body 26. The spool sliding member 30 is coupled to a proximal end 32 of the actuator cable 20, for example, using a clamping mechanism 34. The clamping mechanism 34 preferably includes a cable clamp 36 disposed within the spool sliding member 30 and a thumb screw 38 threadably received in the cable clamp 36 such that the proximal end 32 of the actuation cable 20 is clamped between the cable clamp 36 and the thumb screw 38. Thus, when the spool sliding member 30 slides along the handle body 26 generally in the direction of arrows 35, the actuator cable 20 slides relative to the guide member 18 and actuates, e.g. opens/closes, the instrument head assembly 22, as will be described in greater detail below. The present invention also contemplates other types of cable clamping mechanisms.

The modular medical instrument 10 can be assembled with or without the flush port fitting 14 detachably coupled between the handle body 26 and the guide member 18. In the preferred embodiment, a first coupling member 40 is attached to the proximal end 39 of the guide member 18, and a second coupling member 42 is attached to one end of the flush port fitting 14. When the flush port fitting 14 is used, the flush port fitting 14 is coupled to the first coupling member 40 at the proximal end 39 of the guide member 18 and the second coupling member 42 of the flush port fitting 14 is coupled to a male luer fitting 44 extending from the nose 45 of the handle body 26. When the flush port fitting 14 is not used, the first coupling member 40 at the proximal end 39 of guide member 18 is coupled directly to the luer fitting 44 at the nose 45 of the handle body 26. In the exemplary embodiment, the coupling members 40, 42 include internal threads that engage corresponding external threads on the port fitting 14 and luer fitting 44 respectively.

The flush port fitting 14 includes a flush port 46 having a coupling portion 48 that attaches to a hose or the like for supplying a fluid to the guide member 18. The flush port 46 can be used to flush the guide member 18 with cleaning fluid, thereby facilitating cleaning of the guide member 18. The flush port 46 can also be used during the medical procedure to flush with irrigation fluids or deliver medication to a target location in the patient. A cap can be coupled to the flush port 46 when not in use. The flush port fitting 14 is preferably made of nylon or other sterilizable material, e.g. using autoclave, soak sterilization, and ETO sterilization techniques. The present invention contemplates flush port fittings having any possible shape or design.

The present invention includes various types of instrument devices 2a–2f, FIGS. 2A–2F, having different head assemblies that can be used with the modular medical instrument 10 of the present invention. Each of the instrument devices 2a–2f includes a guide member 18 that can be removably attached to the flush port fitting 14 and/or the handle body 26 and an actuation cable 20 that is clamped by the clamping mechanism 34 of the handle 16.

Figure 2A:
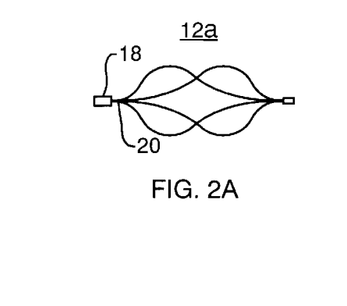
FIGS. 2A–2F are side views of various types of instrument devices that can be used with the modular medical instrument shown in FIG. 1, according to various embodiments of the present invention.
Figures 2B, 2E:
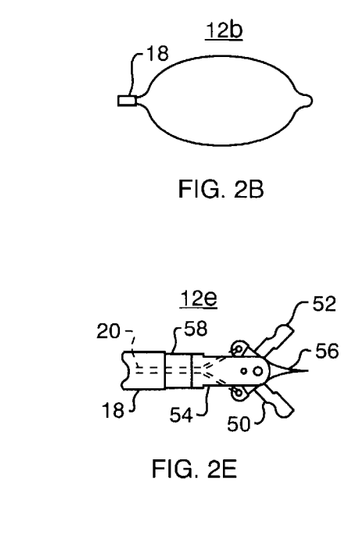
Figures 2C, 2F:
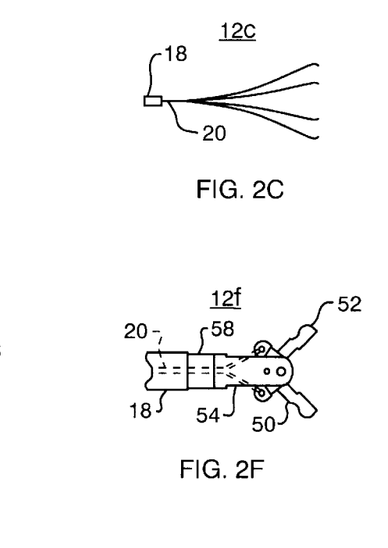
Figure 2D:
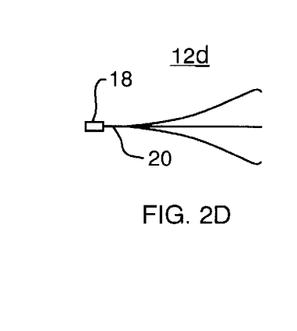

One type of instrument device is formed by the wires forming the actuation cable 20 and includes a four wire helical retrievable basket 12a, FIG. 2A, a snare 12b, FIG. 2B, a four prong grasper 12c, FIG. 2C, and a three prong grasper 2d, FIG. 2D. In each of these instrument devices 2a–2d, the guide member 18 is formed by a TFE extruded outer jacket that allows for fluids to be flushed through. The basket, snare and grasper devices can easily be removed from the guide member 18 for cleaning and/or replacement.

Another type of instrument device includes the biopsy forceps device 12e, 12f, FIGS. 2E and 2F, having a head assembly coupled to the actuation cable 20. The biopsy forceps devices 12e, 12f include jaws 50, 52 pivotably coupled to a body member 54. One type of biopsy forceps device 12e, FIG. 2E, further includes a needle 56 secured to the body member 54 between the jaws 50, 52. An adapter 58 is attached to the stainless steel coil of the guide member 18, for example, using a class VI epoxy, micro-precision crimping, laser welding and/or other suitable techniques that control the amount of heat to prevent annealing in the steel coil of the guide member. The forceps body 54 is detachably coupled to the adapter 58, for example, by threading the body 54 into the adapter 58. The biopsy forceps devices 12e, 12f of the present invention can thus easily be detached from the adapter 58 and disassembled for cleaning and/or replacement of components.

Figure 3:
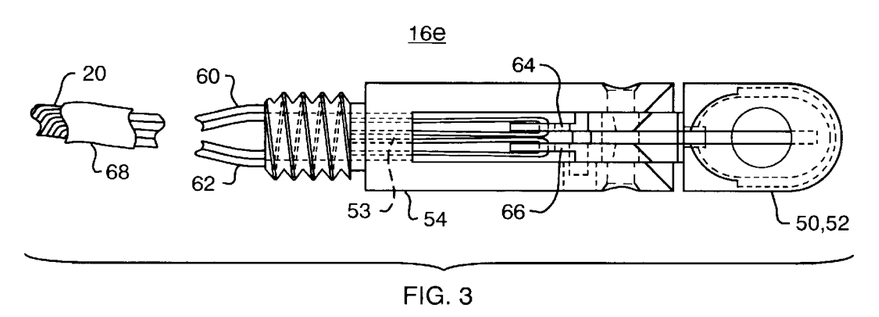
FIG. 3 is a top view of a biopsy forceps device that can be used with the modular medical instrument of the present invention, according to one embodiment of the present invention.
Figure 4A:
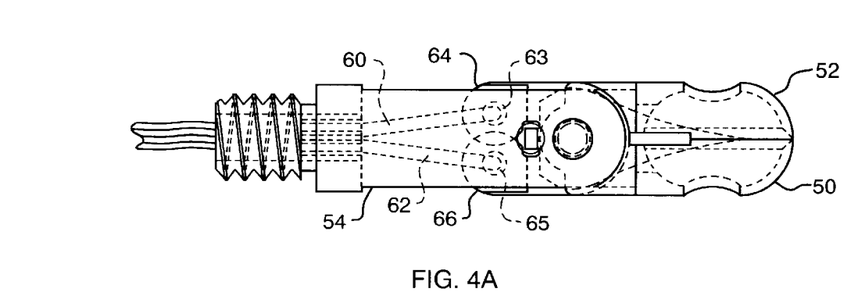
FIGS. 4A and 4B are side views of the biopsy forceps device shown in FIG. 3 in closed and opened positions respectively, according to one embodiment of the present invention.
Figure 4B:
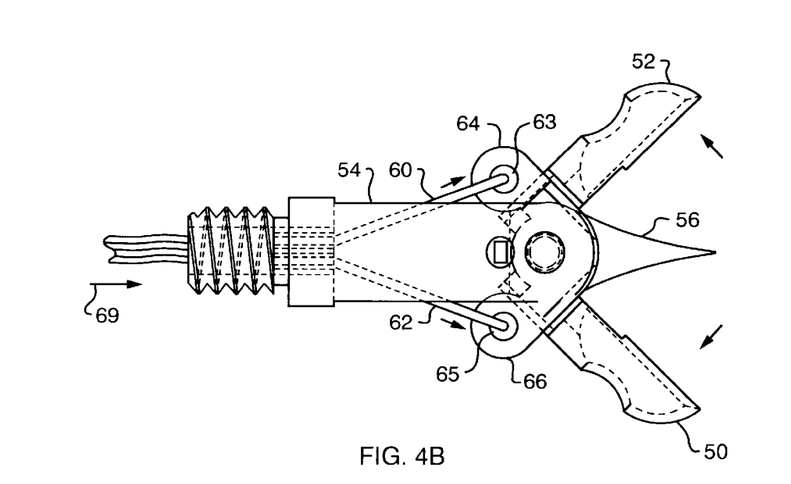

As shown in greater detail in FIGS. 3 and 4A–4B, the jaws are directly coupled to the actuation cable 20, which preferably includes a wound four strand stainless steel cable. Two of the wires 60, 62 from the actuation cable 20 extend through an aperture 53 in the body 54 and loop through holes 63, 65 in the tangs 64, 66 of the jaws 50, 52. These wires 60, 62 are threaded back through the body 54 to the cable 20 and are coupled, for example, with a stainless steel hypotube coupling 68 (FIG. 3) that is crimped with a micro-precision eight position crimp. Movement of the sliding member 30 relative to the handle body 26 causes the actuation cable 20 to move generally in the direction of arrow 69, thereby opening the jaws 50, 52 (FIG. 4B). Moving the sliding member 30 in the opposite direction closes the jaws 50, 52.

Using one continuous stainless steel cable 20 attached to the jaws 50, 52 eliminates the need for the clevis, links and rivets used in the conventional biopsy forceps devices. Also, the wires 60, 62 are preferably not bent in a way that would make the wires susceptible to failure. Furthermore, eliminating the need for brazing or soldering prevents the annealing that causes failure in the guide member 18 or actuation cable 20, increasing the useful life of the biopsy forceps device of the present invention. The present invention contemplates using these novel concepts of attaching the biopsy forceps device to the guide member 18 and actuation cable 20 with other forceps-type assemblies or other types of jaw designs or head assemblies.

In the biopsy forceps embodiments, the guide member 18 is preferably a stainless steel spring coil having an FEP heat shrink outer jacket. The FEP outer jacket provides containment of the fluids being flushed through the inner lumen of the guide member 18 and is able to withstand repeated reprocessing and sterilizations. The FEP outer jacket also provides a smooth and lubricious surface coating that reduces friction when inserted into an endoscope instrument channel. The FEP coating as well as a reduced outer diameter of the guide member 18 improves the tactile feel or "pushability" when pushing the instrument through the instrument channel of the endoscope.

In one example, the outer diameter of the guide member 18 is 0.086 inches (2.2 mm) and the thickness of the FEP outer jacket is about 0.005 inches. In this example, each of the wires 60, 62 have a diameter of about 0.008 inches and extend through an aperture 53 in the body 54 having a diameter of about 0.040 inches and holes 63, 65 in the tangs 64, 66 having a diameter of about 0.0205 inches. In addition to the 2.2 mm biopsy forceps device, the present invention includes other possible sizes, e.g. a 1.8 mm size (an outer diameter of 0.070 inches). Eliminating the clevis and links also reduces the overall length of the head assembly further improving pushability. The preferred embodiment of the biopsy forceps device, however, has elongated the jaws 50, 52 to increase the tissue sample size. For example, the 2.2 mm biopsy forceps device according to the preferred embodiment can obtain a maximum tissue sample of 6.0 mm$^3$.

The present invention also contemplates other types of instrument devices of any possible size including, but not limited to, biopsy forceps with meshing teeth, rat tooth forceps, solid mating tooth retrieval grasping forceps, and a handle that can be plugged into a standard RF generator to allow the instrument device to act as an electrocautery device.

Figure 5:
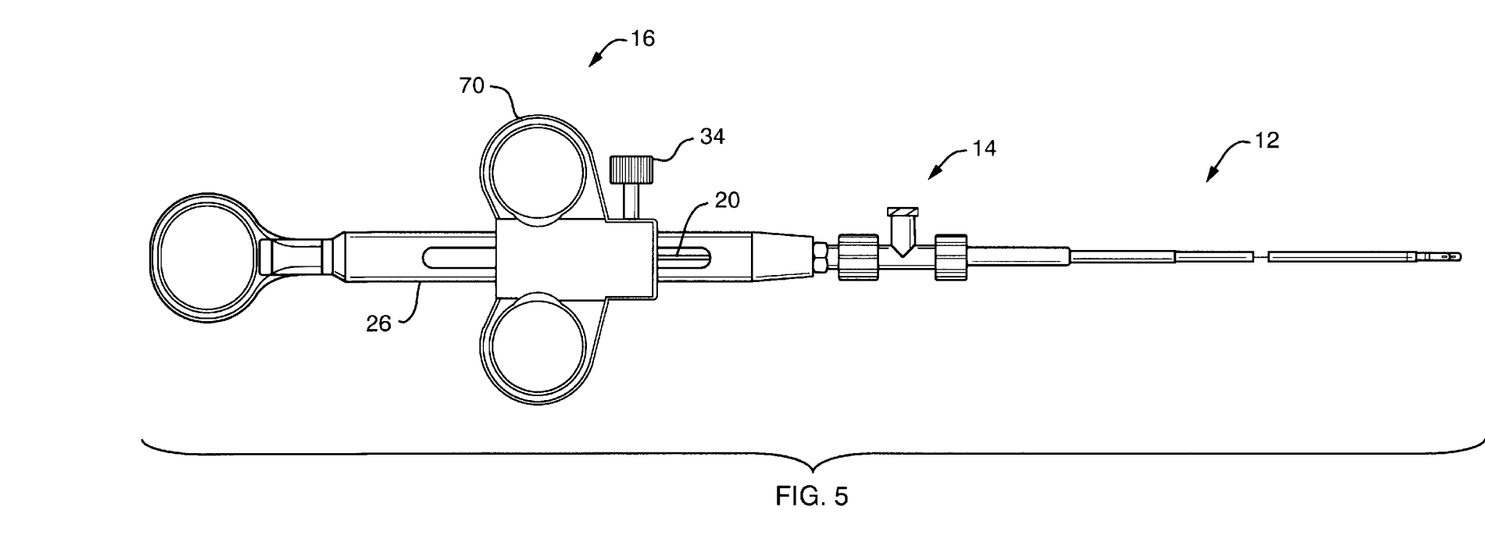
FIG. 5 is a side view of a modular medical instrument, according to another embodiment of the present invention.

According to an alternative embodiment, the actuator handle 16, FIG. 5, includes a two ring finger slide member 70 that slides relative to the handle body 26 and clamps the actuator cable 20 using the clamping mechanism 34. The present invention also contemplates slide member or actuator handles having other shapes or designs.

Figure 6A:
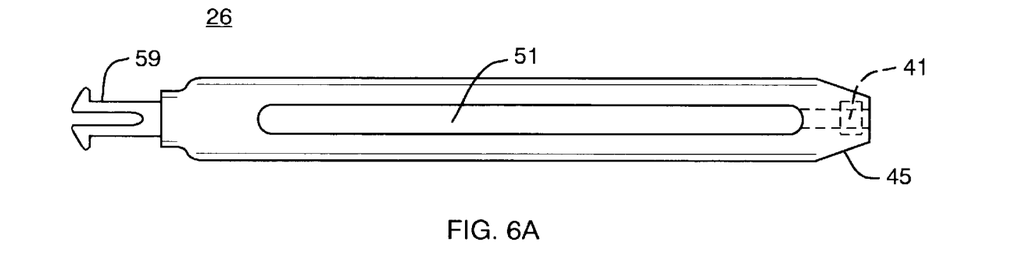
FIG. 6A is a top view of a handle body used in the handle actuator of the modular medical instrument, according to the present invention.
Figure 6B:
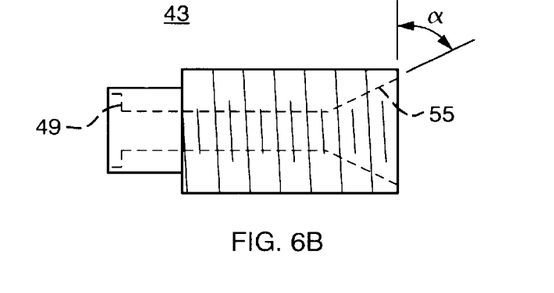
FIGS. 6B and 6C are side and end views, respectively, of a gasket fitting for use in the aperture of the handle body nose, according to the present invention.
Figure 6C:
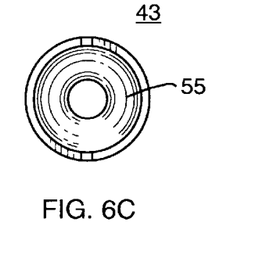
Figure 6D:
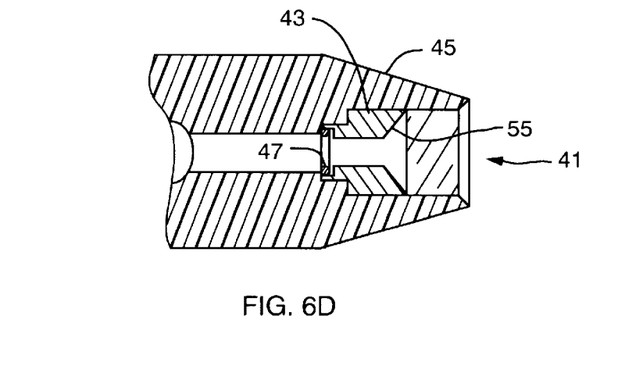
FIG. 6D is an enlarged, cross-sectional view of the gasket fitting disposed in the handle body nose, according to the present invention.

One example of the handle body 26 is shown in greater detail in FIG. 6A. An aperture 41 extends through the nose 45 of the handle body 26 to a slot 51 through the handle body 26. In a preferred embodiment, a gasket fitting 43, FIGS. 6B–6D, is disposed within the aperture 41 extending through the handle nose 45 and behind the luer fitting 44 (see FIG. 1). In one example, the gasket fitting 43 is made of stainless steel. The gasket fitting 43 prevents fluid from being flushed through the handle aperture when the device is being flushed using the flush port fitting . The tapered surface 55 (e.g., having an angle α of about 82°) of the gasket fitting 43 also facilitates centering of the actuation cable 20 into the clamping mechanism 34 during assembly. An O-ring or other similar sealing member 47 is preferably disposed in a counterbore 49 of the gasket fitting 43. The gasket fitting 43 is then screwed into the aperture 41 in the nose 45 of the handle body 26 until the gasket fitting 43 is flush with the bottom of a counterbore in the aperture 41 of the handle body nose 45. The luer fitting 44 is then threaded into the aperture and into abutment with the gasket fitting 43.

Figure 7:
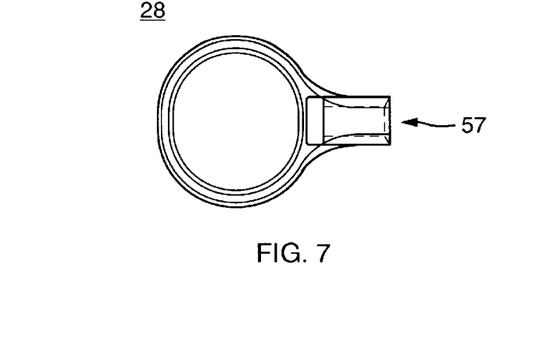
FIG. 7 is a side view of thumb ring used with the handle actuator of the modular medical instrument, according to the present invention.
Figure 8A:
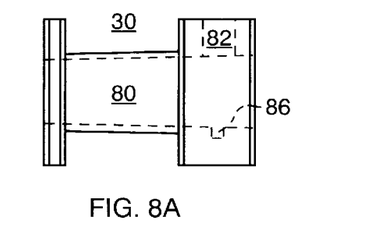
FIGS. 8A and 8B are side and top views, respectively, of a spool sliding member used with a handle actuator of the modular medical instrument, according to the embodiment of the present invention shown in FIG. 1.
Figure 8B:
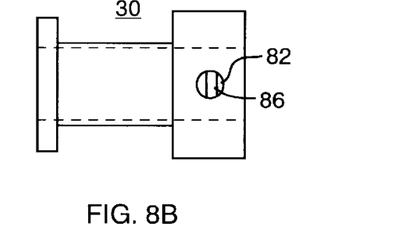
Figure 9A:
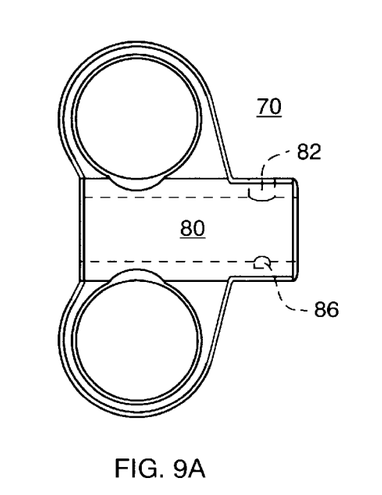
FIGS. 9A and 9B are side and top views, respectively, of the two finger sliding member of the handle actuator used with the modular medical instrument, according to the embodiment of the present invention shown in FIG. 5.
Figure 9B:
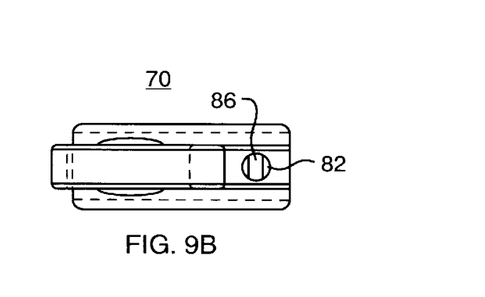

One example of the thumb ring 28 is shown in greater detail in FIG. 7. In the exemplary embodiment, the thumb ring 28 includes a coupling region 57 that receives a coupling member 59 on the handle body 26 (FIG. 6A). An example of the spool slider member 30 used in the embodiment of FIG. 1 is shown in greater detail in FIGS. 8A and 8B. An example of the two ring finger slider member 70 used in the embodiment of FIG. 5 is shown in greater detail in FIGS. 9A and 9B. The spool slider member 30 and the two ring finger slider 70 both include a region 80 extending through the slider members 30, 70 that slidably receives the handle body 26. The handle body 26, thumb ring 28, and slider members 30, 70 are preferably made of a material capable of repeated sterilization using methods, such as autoclave and ETO, or by repeated soak sterilization methods. In one example, the material is a polyetherimide material sold under the name Ultem 1000 by GE Plastics.

Figure 10A:
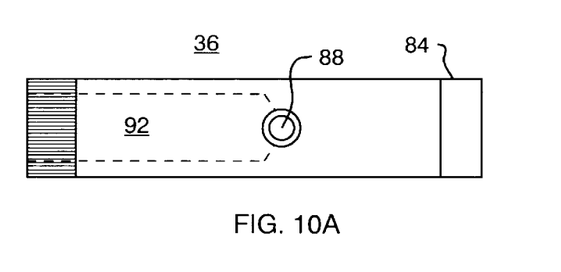
FIGS. 10A and 10B are side and end views, respectively, of a cable clamp used in the handle actuator of the modular medical instrument, according to the present invention.
Figure 10B:
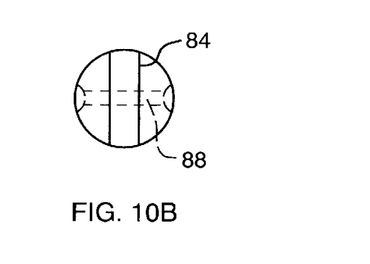

One example of the cable clamp 36 is shown in greater detail in FIGS. 10A and 10B. The cable clamp 36 fits within a hole 82 extending through the slider members 30, 70, and an end portion 84 of the cable clamp 36 engages with a groove 86 opposite the hole 82 in the slider members 30, 70 (FIGS. 8A, 8B, 9A, and 9B). The cable clamp 36 includes through hole 88 for receiving the actuation cable 20. When the slider members 30, 70 are slidably disposed on the handle body 26 (FIG. 6A), the cable clamp 36 extends through the slot 51 in the handle body 26 such that the actuation cable 20 extends through the aperture 41 in the nose 45 of the handle body 26, into the slot 51, and through the hole 88.

Figure 11:
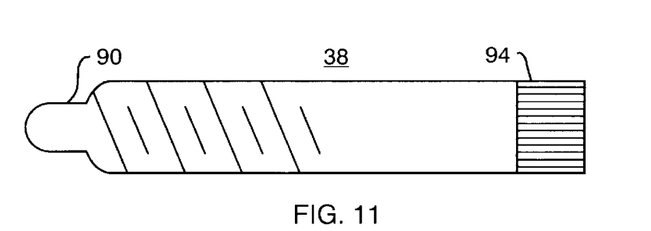
FIG. 11 is a side view of a thumb screw used in the cable clamp of the handle actuator, according to the present invention.
Figure 12:
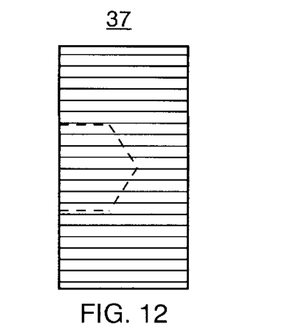
FIG. 12 is a side view of a thumb screw cap used on the thumb screw in the handle actuator of the modular medical instrument, according to the present invention.

One example of the thumb screw 38 is shown in greater detail in FIG. 11. In the exemplary embodiment, the thumb screw 38 is threaded into a region 90 within the cable clamp 36 (FIG. 10A) The thumb screw 38 includes a clamping end 92 that clamps the actuation cable 20 extending through the hole 88 in the cable clamp 36. A knurled thumb screw cap 37, FIG. 12, is preferably attached to the other end 94 of the thumb screw 38 to facilitate threading the thumb screw 38 into and out of engagement with the actuation cable 20. In this example, the cable clamp 36 and thumb screw 38 are preferably made of stainless steel, and the thumb screw cap 37 is preferably made of a polyetherimide material sold under the name Ultem 1000 by GE Plastics.

Figure 13A:
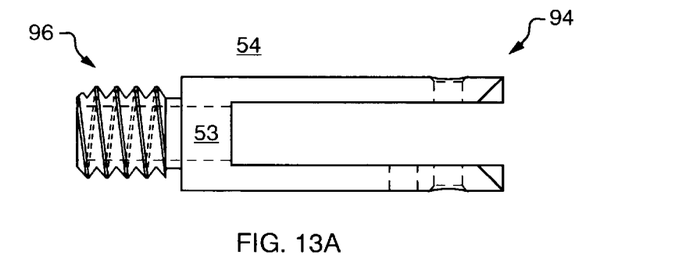
Figure 13B:
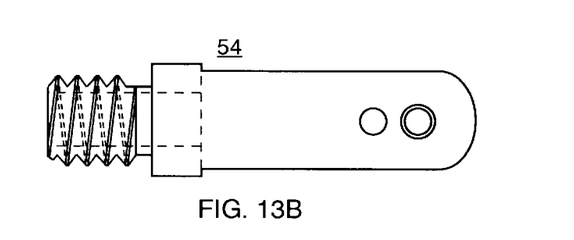

One example of the forceps body 54 is shown in greater detail in FIGS. 13A and 13B. The forceps body 54 includes a first end 94 to which the jaws 50, 52 are pivotably coupled and a second end 96 through which the actuation cable 20 extends (FIG. 3).

Figure 14A:
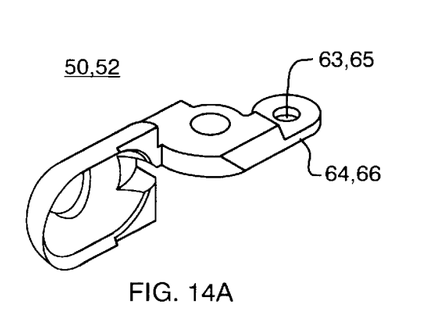
FIGS. 14A and 14B are perspective and side views, respectively, of a jaw of the biopsy forceps device, according to the present invention.
Figure 14B:
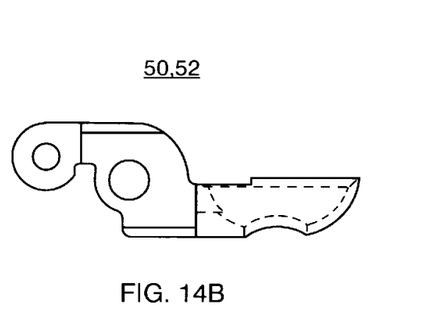
Figure 15:
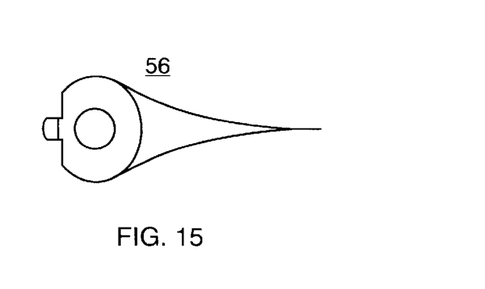
FIG. 15 is a side view of a needle used with a biopsy forceps device, according to one embodiment of the present invention.
Figure 16:
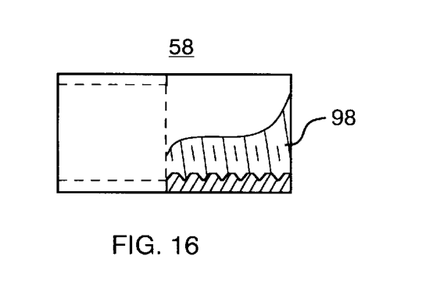
FIG. 16 is a side, partial cross-sectional view of an adapter used to attach a biopsy forceps device to the elongate guide member of the modular medical instrument, according to one embodiment of the present invention.

One example of the jaws 50, 52 is shown in greater detail in FIGS. 14A and 14B. The jaws are preferably made by a drawn stamped process. One example of the needle 56 used in a forceps device 12e (FIG. 2E) is shown in greater detail in FIG. 15. One example of the adapter 58 attached to the guide member 18 for detachably coupling the forceps device is shown in greater detail in FIG. 16. The adapter 58 includes a threaded region 98 that threadably engages the second end 96 of the forceps body 54.

Although specific dimensions and shapes are shown in the exemplary embodiment, the present invention contemplates a modular medical instrument having components of different sizes or shapes. The present invention also contemplates using one or more of the components or features of the present invention with other components or features not expressly disclosed herein.

The modular medical instrument 10 can be provided in either an assembled condition ready for use or in a disassembled condition to be assembled for use. One or more of the components of the modular medical instrument 10 can also be provided separately as replacement parts.

One method for assembling the modular medical device 10 begins by coupling the second coupling member 42 of the flush port fitting 14 to the extension 44 at the nose 45 of the handle body 26. The proximal end 32 of the actuation cable 20 extending out of the proximal end 39 of the guide member 18 is inserted through an aperture in the flush port fitting 14, which centers and guides the cable 20 into the aperture 41 in the nose 45 of the handle body 26 and through the gasket fitting 43 in the nose 45. The flush port fitting 14 is then coupled to the first coupling member at the proximal end 39 of the guide member 18. The proximal end 32 of the actuation cable 20 is then inserted through the hole 88 in the cable clamp 38, thereby positioning the actuation cable 20 in a clamping region between the cable clamp 36 and thumb screw 38 within the sliding member 30, 70. The proximal end 32 of the cable 20 is positioned to a desired location that will allow the jaws 50, 52 or other head assembly to operate, and the thumb screw 38 is tightened to clamp the proximal end 32 of the actuation cable 20. This process can be reversed to disassemble the modular medical instrument 10, for cleaning and/or replacing any one of the component parts.

Accordingly, the modular medical instrument of the present invention can be easily disassembled to facilitate cleaning and/or replacement of any one of the component parts. The modular medical instrument of the present invention is easier to clean and inspect after cleaning, thereby increasing the confidence level of the hospital or medical facility in the sanitation of the medical instruments. The modular medical instrument is also designed to have an extended useful life. Moreover, if the modular medical instrument needs repair, the "take apart" design of the modular medical instrument allows a hospital or medical facility to repair or refurbish the instrument component-by-component without having to return the instrument to the manufacturer. Since the modular medical instruments are more easily cleaned and can be disposed of and replaced on a component-by-component basis, the medical facility will avoid unnecessary medical waste and costs associated with disposing the medical waste. The modular medical instrument according to the present invention also improves the pushability through an instrument channel in an endoscope and prevents excessive wear and damage to the endoscope.

Modifications and substitutions by one ordinary skill in the art are considered to be within the scope of the present invention.

What is claimed is:

1. A modular medical instrument capable of being disassembled for cleaning and reassembled for reuse, said modular medical instrument comprising:

an elongated guide member having a proximal end and a distal end and a channel extending from said proximal end to said distal end;

an inner actuation cable slidably disposed within said channel in said elongated guide member and having a proximal end and a distal end;

an instrument head assembly disposed at said distal end of said inner actuation cable and extending from said distal end of said elongated guide member; and an actuator handle detachably coupled to said proximal end of said elongated guide member and detachably coupled to said proximal end of said inner actuation cable such that said actuator handle moves said inner actuation cable within said channel in said elongated guide member to actuate said instrument head assembly, wherein said actuator handle is capable of being detached and reattached to both said elongated guide member and said inner actuation cable.

2. The modular medical instrument of claim 1 further comprising a port fitting detachably coupled between said proximal end of said elongated guide member and said actuator handle, and wherein said port fitting includes at least one flush port in fluid communication with said channel in said elongated guide member.

3. The modular medical instrument of claim 1 wherein said handle actuator includes:

a handle body having a first end detachably coupled to said proximal end of said elongated guide member, and having a second end, for engagement by a hand of a user; and a sliding member slidably disposed on said handle body, wherein said sliding member is detachably coupled to said proximal end of said inner actuation cable, and wherein said sliding member is adapted to be engaged by said hand of said user such that relative movement between said sliding member and said handle body causes relative movement of said inner actuation cable within said channel of said elongated guide member.

4. The modular medical instrument of claim 1 wherein said instrument head assembly includes:

a body member having a first end and a second end detachably coupled to said distal end of said elongated guide member, wherein said actuation cable extends through said second end of said body member; and first and second forceps jaws pivotably coupled to said first end of said body member, said first and second forceps jaws having respective first and second tangs, wherein said actuation cable has a first portion at one end coupled to said first tang of said first forceps jaw and a second portion at said one end coupled to said second tang of said second forceps jaw, and wherein movement of said actuation cable relative to said body member causes said forceps jaws to open and close.

5. The modular medical instrument of claim 4 wherein said elongated guide member includes an adapter at said distal end of said elongated guide member, and wherein said body member is detachably coupled to said adapter.

6. The modular medical instrument of claim 1 wherein said instrument head assembly includes a grasping device.

7. The modular medical instrument of claim 6 wherein said grasping device is selected from the group consisting of a helical retrieval basket, a snare, a forceps device, and a prong grasper device.

8. The modular medical instrument of claim 3 wherein said activator handle includes a gasket fitting disposed within an aperture in a nose of said handle body and includes a luer fitting disposed within said aperture against said gasket fitting and extending from said nose of said handle body.

9. The modular medical instrument of claim 5 wherein said elongated guide member includes a stainless steel spring coil and an FEP heat shrink outer jacket disposed over said stainless steel spring coil; and wherein said adapter is attached to said stainless steel spring coil.

10. A modular medical instrument assembly capable of being disassembled for cleaning and reassembled for reuse, said modular medical instrument assembly comprising:

an elongated guide member having a proximal end, a distal end and a channel extending from said proximal end to said distal end, said elongated guide member including a coupling member at said proximal end;

a port fitting adapted to be detachably coupled to said coupling member of said elongated guide member, wherein said port fitting includes at least one flush port for providing fluid communication with said elongated guide member and includes a coupling member; and an actuator handle adapted to be detachably coupled to either one of said coupling member of said port fitting and said coupling member of said elongated guide member, wherein said modular medical instrument assembly is capable of being assembled with said port fitting between said actuator handle and said elongated guide member and with said actuator handle directly coupled to said elongated guide member.

11. The modular medical instrument assembly of claim 10 further comprising:

an inner actuation cable adapted to be slidably disposed within said channel of said elongated guide member, wherein said actuator handle is adapted to be detachably coupled to said inner actuation cable; and an instrument device head assembly disposed at a distal end of said inner actuation cable such that said instrument device head assembly extends from said distal end of said elongated guide member when said inner actuation cable is disposed within said channel of said elongated guide member.

12. The modular medical instrument assembly of claim 11 wherein said handle actuator includes:

a handle body having a first end adapted to be detachably coupled to said one of said coupling member of said port fitting and said coupling member of said elongated guide member, and having a second end, for engagement by a hand of a user; and a sliding member slidably disposed on said handle body, wherein said sliding member is adapted to clamp said proximal end of said actuation cable, and wherein said sliding member is adapted to be engaged by said hand of said user such that relative movement between said sliding member and said handle body causes relative movement of said inner actuation cable within said channel of said elongated guide member.

13. The modular medical instrument of claim 11 wherein said instrument head assembly includes a grasping device.

14. The modular medical instrument of claim 11 wherein said instrument head assembly includes:

a body member having a first end and a second end adapted to be detachably coupled to said distal end of said elongated guide member, wherein said actuation cable extends through said second end of said body member; and first and second forceps jaws pivotably coupled to said first end of said body member, said first and second forceps jaws having respective first and second tangs, wherein said actuation cable has a first portion at one end coupled to said first tang of said first forceps jaw and a second portion at said one end coupled to said second tang of said second forceps jaw, and wherein movement of said actuation cable relative to said body member causes said forceps jaws to open and close.

15. The modular medical instrument of claim 14 wherein said elongated guide member includes an adapter at said distal end of said elongated guide member, and wherein said body member is adapted to be detachably coupled to said adapter.

16. A forceps device for use with a modular medical instrument, said forceps device comprising:

a body member having a first end and a second end;

first and second forceps jaws pivotably coupled to said first end of said body member, said first and second forceps jaws having respective first and second tangs; and an actuation cable having at least first and second wires wound together, wherein said first and second wires extend through said second end of said body member, wherein said first wire extends through said first tang of said first forceps jaw and said second wire extends through said second tang of said second forceps jaw, and wherein said first and second wires extend back through said second end of said body member to said actuation cable, wherein movement of said actuation cable relative to said body member causes said forceps jaws to open and close.

17. The biopsy forceps device of claim 16 wherein said actuation cable is a wound stainless steel cable.

18. The forceps device of claim 16 further comprising an elongated guide member, wherein said actuation cable extends through said elongated guide member and wherein said body member is detachably coupled to one end of said elongated guide member.

19. The forceps device of claim 18 wherein said elongated guide member includes a stainless steel spring coil and an FEP heat shrink outer jacket disposed over said stainless steel spring coil.

20. The modular medical instrument of claim 19 wherein said elongated guide member includes an adapter secured to said stainless steel spring coil at said distal end of said elongated guide member, and wherein said body member is detachably coupled to said adapter.

\* \* \* \* \*